United States Patent [19]
Abraham et al.

[11] Patent Number: 4,992,659
[45] Date of Patent: Feb. 12, 1991

[54] NEAR-FIELD LORENTZ FORCE MICROSCOPY

[75] Inventors: David W. Abraham, Ossining; Hemantha K. Wickramasinghe, Chappaqua, both of N.Y.

[73] Assignee: International Business Machines Corporation, Armonk, N.Y.

[21] Appl. No.: 386,330

[22] Filed: Jul. 27, 1989

[51] Int. Cl.$^5$ .................................... G01R 33/30
[52] U.S. Cl. .................... 250/306; 250/307; 324/158 R
[58] Field of Search .................... 250/306, 307; 324/158 R

[56] References Cited

U.S. PATENT DOCUMENTS

| | | | |
|---|---|---|---|
| 3,535,515 | 10/1970 | Jones et al. | 250/49.5 |
| 4,343,993 | 8/1982 | Binnig et al. | 250/306 |
| 4,668,865 | 5/1987 | Gimzewski et al. | 250/306 |
| 4,677,474 | 6/1987 | Sato et al. | 324/158 R |
| 4,837,435 | 6/1989 | Sakuhara et al. | 250/306 |
| 4,861,990 | 8/1989 | Coley | 250/306 |
| 4,864,227 | 9/1989 | Sato | 324/158 R |
| 4,874,945 | 10/1989 | Ohi | 250/306 |

FOREIGN PATENT DOCUMENTS

62-89483  2/1987  Japan.

OTHER PUBLICATIONS

C. M. Mate, "Atomic Scale Friction of a Tungsten Tip on a Graphite Surface", IBM Research Report RJ5828 dated 9/11/87.
Abstract of EP-239085A.
Martin et al., "Magnetic Imaging by Force Microscopy with 1000 Å Resolution", Appl. Phys. Lett., vol. 50, No. 20, May 1987, pp. 1455–1457.
Celotta et al., "Polarized Election Probes of Magnetic Surfaces", Science, vol. 234, Oct. 1986, pp. 333–340.
Martin et al., "Atomic Force Microcope-Force Mapping and Profiling on a Sub 100-Å Scale", J. Appl. Phys. 61 (10), May 1987, pp. 4723–4729.
Young et al., "The Topografiner: An Instrument for Measuring Surface Microtopography", The Review of Scientific Instruments, vol. 43, No. 7, Jul. 1972, pp. 999–1011.
Durig et al., "Force Sensing in Scanning Tunneling Microscopy", IBM Research Report, RZ1513, 9/17/86.

*Primary Examiner*—Jack I. Berman
*Assistant Examiner*—Kiet T. Nguyen
*Attorney, Agent, or Firm*—Philip J. Feig

[57] ABSTRACT

Magnetic structures of a sample are imaged by measuring Lorentz force-induced deflection of the tip of a scanning tunneling microscope. While scanning the sample, an a.c. voltage signal at a first predetermined frequency equal to the resonance frequency of the tip is applied to the tip for generating a current between the tip and the surface of the sample for causing the tip to undergo vibratory motion relative to the sample. The tip motion, indicative of the presence of a magnetic field, is optically detected. In an alternative embodiment for providing improved resolution the tip is made to undergo motion at a second predetermined frequency in a direction parallel to the longitudinal axis of the tip and normal to the surface of the sample. The tip motion is optically detected at the sum or difference frequency of the first and second predetermined frequencies for providing improved lateral resolution of the magnetic field measurements using a scanning tunneling microscope. In the alternative embodiment the sum or difference frequency, which ever is detected, is made equal to the resonance frequency of the tip. The magnetic field measurement and tip position are provided to a computer which, in turn, provides an output signal to a device for providing a graphical representation of the magnetic field at different positions on the surface of the sample.

50 Claims, 1 Drawing Sheet

NEAR-FIELD LORENTZ FORCE MICROSCOPY

BACKGROUND OF THE INVENTION

The present invention concerns Lorentz force microscopy and in particular concerns imaging magnetic structures in a sample with high resolution by measuring Lorentz force-induced deflection of the tip in a scanning tunneling microscope (STM).

Several approaches exist for imaging magnetic field distributions on a microscopic scale. For moderate resolutions optical techniques based upon the Kerr effect are adequate and provide spatial resolution of approximately 0.5 micron which is limited by the optical wavelength. Another approach is to use the Bitter pattern technique which requires the spreading of a magnetic particle suspension over the surface to be imaged and subsequently obtaining an image using light. In order to achieve higher spatial resolution, it is necessary to resort to the use of electron beam imaging techniques such as spin polarized imaging and Lorentz microscopy.

Presently, leading techniques for high-resolution imaging of magnetic structures include the use of magnetic force microscopy (MFM) as is described in the article by Y. Martin and H.K. Wickramasinghe entitled "Magnetic Imaging by "Force Microscopy" with 1000 Å Resolution", *Appl. Phys. Lett* Vol. 50, No. 20, May 18, 1987, pp. 1455–1457, in which the lateral resolution is limited by the tip size, typically 1000 angstroms. Another technique is the use of scanning electron microscopy with polarization analysis (SEMPA) as is described in the article by R.T. Celotta and D.T. Pierce entitled "Polarized Electron Probes of Magnetic Surfaces", *Science,* Vol. 234, Oct. 17, 1986, pp. 333–340, which in principle is limited in resolution to the far-field electron beam spot size. The SEMPA technique also suffers from the difficulties associated with surface preparation and in the reliability of the polarization-sensitive detector. To date, the SEMPA technique has been demonstrated with a resolution of 1000 angstroms, but the potential exists of achieving 100 angstroms resolution.

The present invention provides for accurate measurement of the force between a tip and a sample as a function of the spacing between the tip and sample surface. A tip is vibrated in close proximity to &he surface and an optical heterodyned interferometer is employed to accurately measure the vibration of the tip. The technique provides a sensitive and flexible arrangement for measuring the force. As a result, it is possible to image the magnetic field by noncontact profiling on a scale of a few angstroms.

Specifically, the measuring technique of the present invention is theoretically capable of attaining resolution which is limited only by the near-field beam size, i.e. better than 5 angstroms lateral resolution, as demonstrated using high-resolution images of a scanning tunneling microscope.

In accordance with the teachings of the present invention, a scanning tunneling microscope is operated using a long, thin tip. In such a configuration the tip is stiff in a direction normal to the plane of the sample surface but is flexible in a direction parallel to the plane of the sample surface. In the presence of a magnetic field in a plane parallel to the sample surface, and with a tunneling current passing between the tip and the sample, there will be a static deflection of the tip. When applying a first alternating current bias voltage at a first frequency between the tip and sample, the oscillatory current causes the tip to undergo vibratory motion at the first frequency in a direction parallel to the sample surface. The oscillatory motion is detected by means of an optical heterodyned interferometer by measuring the laser phase variations.

The motion of the tip may be detected in two orthogonal planes, which as will be described hereinafter determine the magnitude and direction of the component of the magnetic field parallel to the sample surface. The detection is accomplished, for example, either by using two, independent interferometers or by using a simple interferometer and measuring both the amplitude and phase of the detected optical signal. By scanning the tip across the sample surface, an image of the vector magnetic field throughout the sample is thus obtainable.

Scanning tunneling microscopes are well known and are described, for example, in U.S. Pat. No. 4,343,993 entitled "Scanning Tunneling Microscope", issued to G. Binnig et al and assigned to the same assignee as the present invention, which patent is incorporated herein by reference.

SUMMARY OF THE INVENTION

A principal object of the present invention is therefore, the provision of an apparatus for and a method of imaging magnetic structures in a sample with high resolution by measuring the Lorentz force-induced deflection of the tip in a scanning tunneling microscope.

Another object of the invention is the provision of an apparatus for and a method of imaging magnetic structures in a sample in which the resolution is in the order of approximately several angstroms.

A further object of the invention is the provision of an apparatus for and a method of simultaneously measuring the topography and lateral field strength of a sample.

Further and still other objects of the invention will become more clearly apparent when the following description is read in conjunction with the accompanying drawing.

DETAILED DESCRIPTION

Figure 1:
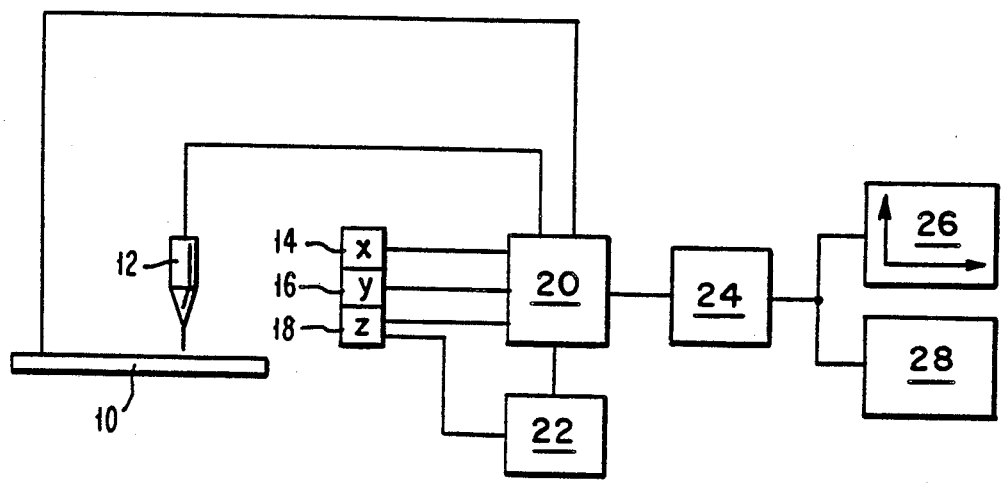
FIG. 1 is a schematic representation of the essential components of a conventional scanning tunneling microscope.

Referring now to the figures and to FIG. 1 in particular there is shown schematically the essential components of a conventional scanning tunneling microscope. A sample 10 to be imaged acts as an electrode above which and in close proximity thereto a tip 12 is disposed. The sample and tip are capable of undergoing motion relative to each other in each of the three coordinate axes designated x, y and z. The sample and/or the tip are also provided with three piezoelectric drives 14, 16, 18. Piezoelectric drives 14 and 16 operate in the lateral directions x and y respectively. The drives may act either on the tip 12, the sample 10 or a combination of both to cause relative motion between the tip and sample along the x and y axes. Vertical piezoelectric drive 18 adjusts the spacing between the tip 12 and surface of sample 10 in the z-axis direction, in the vertical direction as shown. A measuring device 20 is coupled to sample 10 and tip 12 as well as to piezoelectric drives 14, 16 and 18. Controller 22 is coupled both to measuring device 20 and z-axis piezoelectric drive 18 for controlling the separation distance between the sample 10 and tip 12. Measuring device 20 is connected to analyzer 24 which in turn is connected to an output device such as a plotter 26 or a viewing screen 28. The electrodes are drawn schematically in exaggerated size. The actual mechanical dimensions of the electrodes, sample and tip, as well as their possible range of adjustment are extraordinarily small because of the delicate nature of the tunneling effect. The controller 22 must be able to operate very precisely and the measuring device 20 must be extremely sensitive.

Figure 2:
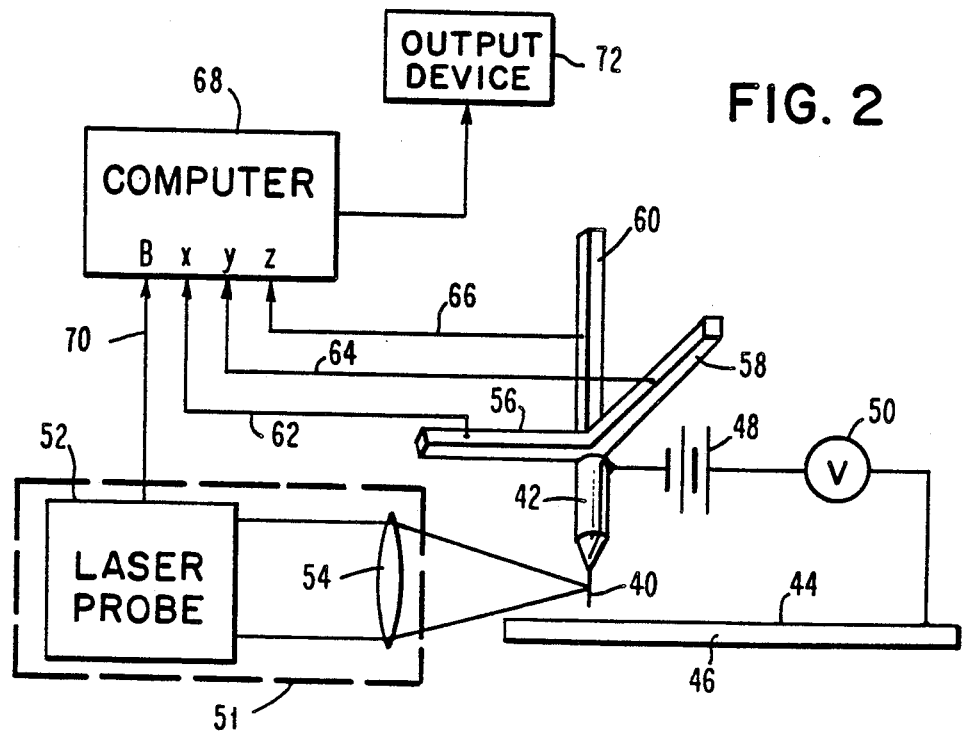
FIG. 2 is a schematic representation of an apparatus useful for practicing the present invention.

The present invention provides a measurement resolution of better than 5 angstroms in a lateral direction. As shown in FIG. 2, a scanning tunneling microscope is operated using a long thin tip 40 supported by support 42. The tip 40 is rigid in a direction along the longitudinal axis of the tip, i.e. in a direction substantially normal to the surface 44 of a metallic sample 46, and is flexible in a direction substantially parallel to the sample surface 44. The tip, preferably fabricated from tungsten, is dimensioned approximately 200 microns in length with a diameter tapering from 10 microns at the base to a final point approximately 20 nanometers in diameter.

When a magnetic field is manifest in the plane of the sample and a current from source 48 is passed between the tip 40 and sample 46, there will be a static deflection in the direction $\vec{r} = \vec{I} \times \vec{B}$. When applying an a.c. bias voltage at a frequency $\omega_1$ from a voltage generator 50 between the tip 40 and sample 46, the operating current causes the tip 40 to undergo vibratory motion in a direction substantially parallel to the plane of the sample surface 44. The motion of the tip 40 is detected and measured using an optical heterodyned interferometer 51 comprising laser probe 52 and lens 54.

Optical heterodyned interferometers are known. A preferred interferometer which has been used successfully in applications with a scanning force microscope is described in detail in the article "Atomic Force Microscope-Force Mapping and Profiling on a sub 100-Å Scale" by Y. Martin, C.C. Williams and H.K. Wickramasinghe, J. Appl. Phys., Vol. 61, No. 10, May 15, 1987, pages 4723-4729, which article is incorporated herein by reference. The tip 40 and holder 42 are coupled to x, y and z piezoelectric drives shown schematically as elements 56, 58, and 60 respectively. The position of the tip relative to a point on the stationary sample 46 in the x, y and z directions respectively is provided along conductors 62, 64, and 66 to a computer 68. While the tip is scanned over the sample in the x-axis and y-axis direction, the position calculated by computer 68 from the piezoelectric drive signals received from each of the element 56, 58 and 60 along conductors 62, 64 and 66 respectively and the magnetic field strength B provided from the interferometer 51 along conductor 70 to the computer 68 are combined to generate at an output device 72 a representation of the magnetic field along the surface of the sample 46 as the tip is scanned over the surface. The output device 72 may be a screen presentation, plotter, recorder or any other device capable of providing a graphical or tabular representation of the magnetic field as a function of position along the surface 44 of the sample 46.

In operation, the tip is located at a distance in the order of one nanometer from the surface of the sample. The amplitude of the vibratory motion is in the range between 0.1 to 10 nanometers. The computer 68 is preferably an IBM PC/AT or a computer of equal or better capability for data acquisition.

While the above description discloses motion of the tip relative to a stationary sample, it will be apparent to those skilled in the art that relative motion between a stationary tip and moving sample or between a moving tip and moving sample, as described in conjunction with the description of the STM shown in FIG. 1, will perform equally as well.

The magnitude of the magnetic field effect is calculable by the computer 68 as follows. In a material with a magnetic field B located just outside of the sample which decreases over a characteristic length scale l exhibiting a tunnel current I, and where the spring constant of the tip 40 is k, the static deflection of the tip is in the order of IBl/k. For the case of an alternating current current having a frequency $\omega_1$ of the bias voltage selected to be approximately equal to the mechanical resonance frequency of the tip, the amplitude a of the tip motion is Q multiplied by the static deflection or a=QIBl/k. In the case of high spatial frequency components of the magnetic field, the length l over which the magnetic field B decays is approximately equal to the spatial wavelength of B. Therefore, in order to resolve 100 angstrom fluctuations of the tip in the field B, l is set to 100 angstroms. For a typical Q of 100, $B=1W/m^2$, $k=10^{-2}N/m$, an alternating current of 1μA and l=100 angstroms, the tip will oscillate at a peak-to-peak amplitude of 1 angstrom. The intrinsic limit of resolution of the microscope for magnetic field imaging will be similar to that of a scanning tunneling microscope, possibly being limited by increased tunneling area and gap distance due to field emission from the tip. Both of these effects are known to be several orders of magnitude below the resolution available with currently known techniques. These effects are described, for instance, in the article entitled "The Topografiner: An Instrument for Measuring Surface Microtopography" by R. Young, J. Ward and F. Scire, Rev. Sci. Instr., Vol. 43, No. 7, July 1972, pages 999-1011.

The signal-to-noise ratio of the measurement is determined by the noise limit of the optical interferometer and by thermally excited oscillation of the tip. Tests have shown that the optical interferometer described in the Martin et al article supra is able to measure tip displacements as low as approximately $5 \times 10^{-5} \text{Å}/\sqrt{Hz}$ for 100μW of laser power and therefore does not represent a severe limitation. For a spring constant of $10^{-2}N/m$, the root-mean-square fluctuation in tip position is approximately 12Å at room temperature. The amplitude in a bandwidth β is given by the expression $N=(4R_B TQ\beta/k\omega_1)^{\frac{1}{2}}$. When attempting to achieve 100 angstroms resolution (i.e., a=1) with the parameters set forth hereinabove, the bandwidth β and the resonant frequency $\omega_1$ of the tip 40 are related as follows: $\omega_1/\beta = 1.6 \times 10^4$ in order to achieve a signal-to-noise ratio of 1. Typically, $\omega_1$ is approximately 50 kHz, so that β is approximately 4 Hz. The practical limit to measurement resolution will then be due to drift in the scanning tunneling microscope, which sets a lower bound on β of approximately 0.1 Hz to 1 Hz, or roughly 15Å resolution.

Further immunity from environmental noise sources is achievable by vibrating the tip at a second frequency $\omega_2$ in a direction along the z-axis, substantially normal to the plane of the surface 44 of the sample 46. The tip is made to undergo vibratory motion by applying a suitable a.c. voltage signal to the z-axis piezoelectric drive. The frequency $\omega_2$ is not at the resonant frequency of the tip and $\omega_2$ so that the sum or difference frequency, which ever is detected, is at the resonance frequency of the tip. A typical value for $\omega_2$ is between 10 kHz and 100 kHz. Detection of the tip motion by the optical heterodyned interferometer at a difference or sum frequency of the two applied motions ($\omega_1 \pm \omega_2$) results in the interaction of only the tip 40 and sample 46 being detected and measured. In addition to rejecting low resolution components of the force interaction with the tip, the described heterodyned scheme eliminates spurious signals resulting from Joule heating-induced modulation of the sample height. Either a single interferometer, as shown, capable of measuring laser phase variations or two interferometers, each measuring motion along one of the axes of motion, measure the tip motion.

While the above refers to motion of the tip, it will be apparent to those skilled in the art that the relative motion between the tip and sample is important. Therefore, motion of the tip, sample or both the tip and sample may be used in practicing the present invention.

The tip motion and x, y and z axes position are provided to the computer as described above. The computer, in turn, calculates the magnetic field strength at each associated tip position relative to the sample surface, using the above described equation relating tip vibration amplitude and field strength and provides an output signal responsive to the calculated values.

The above described invention offers unique advantages over the prior methods. First, the apparatus operates independently as a conventional scanning tunneling microscope. Thus, the topography and lateral magnetic field strength are measured simultaneously. Since the static deflection of the tip (for topographical measurement) is quite small compared to the length scales of interest, the topography and magnetic field image is readily separated. Therefore, an independent measure of magnetic field strength, apart from the topographic measurement, is conveniently achieved. Second, the resolution is much better than that achieved using either magnetic force microscopy or scanning electron microscopy with polarization analysis since the better high resolution obtainable with the scanning tunneling microscope determines resolution of the magnetic field measurement. Tip shape affects resolution in the same manner as in a conventional scanning tunneling microscope, particularly when measuring rough surfaces. Also, secondary election emission will not play a large role in the resolution limit. Finally, by detecting the tip oscillation in two orthogonal directions, the direction of magnetization in the sample can be determined.

While there has been described and illustrated a method and preferred embodiment of an apparatus for measuring the magnetic field strength of a sample, it will be apparent to those skilled in the art that modifications and variations thereof are possible without deviating from the broad spirit of the invention which shall be limited solely by the scope of the claims appended hereto.

What is claimed is:

1. An apparatus for measuring a magnetic field in a sample using a scanning tunneling microscope having a tip comprising:
    drive means for controlling the distance between the tip and a surface of the sample and a position of the tip for enabling scanning of the surface and for providing a signal indicative of the position of the tip relative to the sample;
    generator means coupled to said tip for providing a current signal at a frequency substantially equal to the resonance frequency of said tip for generating a current between said tip and the surface for causing the tip to undergo vibratory motion in the presence of a magnetic field;
    detector means disposed for measuring the motion of the tip in a direction substantially parallel to the plane of the surface of the sample and providing a signal indicative of such motion, and
    computer means coupled to said detector means and said drive means for providing an output signal indicative of a position of the tip and a magnetic field magnitude corresponding to the position.

2. An apparatus as set forth in claim 1 further comprising output device means coupled to said computer means for providing an image of the magnetic field magnitude at corresponding positions of the tip.

3. An apparatus as set forth in claim 2, wherein said output device means comprises a screen.

4. An apparatus as set forth in claim 2, wherein said output device means comprises a plotter.

5. An apparatus as set forth in claim 1, wherein said drive means comprises piezoelectric drive means for positioning the tip relative to the surface.

6. An apparatus as set forth in claim 5, wherein said piezoelectric drive means positions the tip relative to a stationary surface.

7. An apparatus as set forth in claim 5, wherein said piezoelectric drive means position the surface relative to a stationary tip.

8. An apparatus as set forth in claim 1, wherein said computer means provides another output indicative of the topography of the surface of the sample.

9. An apparatus as set forth in claim 1, wherein said detector means is an optical heterodyned interferometer.

10. A method for measuring a magnetic field in a sample using a scanning tunneling microscope having a tip comprising the steps of:
    disposing the tip in close proximity to a surface of a sample and scanning the surface;
    providing to the tip a current signal at a frequency substantially equal to the resonance frequency of the tip for generating a current between the tip and the surface for causing the tip to undergo vibratory motion in the presence of a magnetic field;
    measuring the motion of the tip in a direction substantially parallel to the plane of the surface of the sample and providing a signal indicative of such motion, and
    computing the position of the tip and a magnetic field magnitude corresponding to the position.

11. A method as set forth in claim 10, further comprising the step of displaying the position of the tip and the magnetic field magnitude corresponding to the tip position.

12. A method as set forth in claim 10, further comprising the step of simultaneously measuring the topography of the surface of the sample.

13. A method as set forth in claim 12, further comprising the step of simultaneously displaying the topography of the surface of the sample.

14. A method as set forth in claim 10, wherein said measuring the motion is optically measuring the motion.

15. An apparatus for measuring a magnetic field in a sample using a scanning tunneling microscope having a tip comprising:
- piezoelectric drive means for controlling the distance between the tip and a surface of the sample and a position of the tip for enabling scanning of the surface and providing a signal indicative of the position of the tip;
- generator means for providing a current at a frequency substantially equal to the resonance frequency of the tip for generating a current signal between the tip and the surface of the sample for causing the tip to undergo vibratory motion in the presence of a magnetic field;
- optical heterodyned interferometric means disposed for measuring the motion of the tip in a direction substantially parallel to the plane of the surface of the sample and providing a signal indicative of such motion;
- computer means coupled to said optical heterodyned interferometric means and said piezoelectric drive means for providing an output signal indicative of a position of the tip and a magnetic field magnitude corresponding to the position, and
- output device means for providing a display responsive to said output signal.

16. An apparatus as set forth in claim 15 said computer means providing another output signal indicative of the topography of the surface of the sample.

17. An apparatus for measuring a magnetic field in a sample using a scanning tunneling microscope having a tip comprising:
- drive means for controlling the distance between the tip and a surface of the sample and a position of the tip for enabling scanning of the surface and for providing a signal indicative of the position of the tip relative to the sample;
- generator means coupled to the tip for providing a current signal at a first predetermined frequency for generating a current between the tip and the surface for causing the tip to undergo vibratory motion in the presence of a magnetic field;
- means coupled to said drive means for causing the tip to undergo vibratory motion relative to the surface at a second predetermined frequency along an axis substantially normal to the plane of the surface of the sample;
- detector means disposed for measuring the motion of the tip in a direction substantially parallel to the plane of the surface of the sample and providing a signal indicative of such motion, and
- computer means coupled to said detector means and said drive means for providing an output signal indicative of a position of the tip and a magnetic field magnitude corresponding to the position.

18. An apparatus as set forth in claim 17 further comprising output device means coupled to said computer means for providing an image of the magnetic field magnitude at corresponding positions of the tip.

19. An apparatus as set forth in claim 18, wherein said output device means comprises a screen.

20. An apparatus as set forth in claim 18, wherein said output device means comprises a plotter.

21. An apparatus as set forth in claim 17, wherein said drive means comprises piezoelectric drive means for positioning the tip relative to the surface.

22. An apparatus as set forth in claim 21, wherein said piezoelectric drive means positions the tip relative to a stationary surface.

23. An apparatus as set forth in claim 21, wherein said piezoelectric drive means position the surface relative to a stationary tip.

24. An apparatus as set forth in claim 17, wherein said detector means is an optical heterodyned interferometer means.

25. An apparatus as set forth in claim 17, wherein said detector means measures the motion of the tip at a sum frequency substantially equal to the sum of said first predetermined frequency and said second predetermined frequency and the sum frequency is substantially equal to the resonance frequency of the tip.

26. An apparatus as set forth in claim 25 wherein said detector means is an optical heterodyned interferometer means.

27. An apparatus as set forth in claim 17, wherein said detector means measures the motion of the tip at a difference frequency substantially equal to the difference of said first predetermined frequency and said second predetermined frequency and the difference frequency is substantially equal to the resonance frequency of the tip.

28. An apparatus as set forth in claim 27 wherein said detector means is an optical heterodyned interferometer means.

29. An apparatus as set forth in claim 17, wherein said computer means provides another output indicative of the topography of the surface of the sample.

30. A method for measuring a magnetic field in a sample using a scanning tunneling microscope having a tip comprising the steps of:
- disposing the tip in close proximity to a surface of a sample and scanning the surface;
- providing to the tip a current signal at a first predetermined frequency for generating a current between the tip and the surface for causing the tip to undergo vibratory motion in the presence of a magnetic field;
- simultaneously vibrating the tip at a second predetermined frequency along an axis substantially normal to the plane of the surface of the sample;
- measuring the motion of the tip in a direction substantially parallel to the plane of the surface of the sample and providing a signal indicative of such motion, and
- computing the position of the tip and a magnetic field magnitude corresponding to the position.

31. A method as set forth in claim 30 further comprising the step of displaying the position of the tip and the magnetic field magnitude corresponding to the tip position.

32. A method as set forth in claim 30, further comprising the step of simultaneously measuring the topography of the surface of the sample.

33. A method as set forth in claim 32, further comprising the step of simultaneously displaying the topography of the surface of the sample.

34. A method as set forth in claim 32 wherein said measuring is optical measuring.

35. A method as set forth in claim 30 wherein said measuring measures the motion of the tip at a sum frequency substantially equal to the sum of said first predetermined frequency and said second predetermined frequency and the sum frequency is substantially equal to the resonance frequency of the tip.

36. A method as set forth in claim 35 wherein said measuring is optical measuring.

37. A method as set forth in claim 30 wherein said measuring measures the motion of the tip at a difference frequency substantially equal to the difference between said first predetermined frequency and said second predetermined frequency and the difference frequency is substantially equal to the resonance frequency of the tip.

38. A method as set forth in claim 37 wherein said measuring is optical measuring.

39. An apparatus for measuring a magnetic field in a sample using a scanning tunneling microscope having a tip comprising:
  piezoelectric drive means for controlling the distance between the tip and a surface of the sample and a position of the tip for enabling scanning of the surface and providing a signal indicative of the position of the tip;
  generator means coupled to the tip for providing a current signal at a first predetermined frequency for generating a current between the tip and the surface for causing the tip to undergo vibratory motion in the presence of the magnetic field;
  means coupled to said piezoelectric drive means for causing the tip to undergo vibratory motion at a second predetermined frequency along an axis substantially normal to the plane of the surface of the sample;
  optical heterodyned interferometric means disposed for measuring the motion of the tip in a direction substantially parallel to the plane of the surface of the sample and providing a signal indicative of such motion;
  computer means coupled to said optical heterodyned interferometric means and said piezoelectric drive means for providing an output signal indicative of a position of the tip and a magnetic field magnitude corresponding to the position, and
  output drive means for providing a display responsive to said output signal.

40. An apparatus as set forth in claim 39 said computer means providing another output signal indicative of the topography of the surface of the sample.

41. An apparatus as set forth in claim 39 wherein said optical heterodyned interferometric means measures the motion of the tip at a sum frequency substantially equal to the sum of said first predetermined frequency and said second predetermined frequency and said sum frequency is substantially equal to the resonance frequency of the tip.

42. An apparatus as set forth in claim 39 wherein said optical heterodyne means measures the motion of the tip at a difference frequency substantially equal to the difference between said first predetermined frequency and said second predetermined frequency and said difference frequency is substantially equal to the resonance frequency of the tip.

43. An apparatus for measuring a magnetic field in a sample using a scanning tunneling microscope having a tip comprising:
  drive means for controlling the distance between the tip and a surface of the sample and a position of the tip for enabling scanning of the surface and for providing a signal indicative of the position of the tip relative to the sample;
  generator means coupled to said tip for providing a signal for generating a current between said tip and the surface;
  detector means disposed for measuring the motion of the tip in a direction substantially parallel to the plane of the surface and providing a signal indicative of such motion, and
  computer means coupled to said detector means and said drive means for providing an output signal indicative of a position of the tip and a magnetic field magnitude corresponding to the position.

44. An apparatus as set forth in claim 43 further comprising output device means coupled to said computer means for providing an image of the magnetic field magnitude at corresponding positions of the tip.

45. An apparatus as set forth in claim 43, wherein said computer means provides another output indicative of the topography of the surface of the sample.

46. An apparatus as set forth in claim 43, wherein said detector means is an optical heterodyned interferometer.

47. A method for measuring a magnetic field in a sample using a scanning tunneling microscope having a tip comprising the steps of:
  disposing the tip in close proximity to a surface of a sample and scanning the surface;
  providing to the tip a signal for generating a current between the tip and the surface;
  measuring the motion of the tip in a direction substantially parallel to the plane of the surface and providing a signal indicative of such motion, and
  computing the position of the tip and a magnetic field magnitude corresponding to the position.

48. A method as set forth in claim 47, further comprising the step of displaying the position of the tip and the magnetic field magnitude corresponding to the tip position.

49. A method as set forth in claim 47, further comprising the step of simultaneously measuring the topography of the surface of the sample.

50. A method as set forth in claim 49, further comprising the step of simultaneously displaying the topography of the surface of the sample.

* * * * *